United States Patent [19]

Bank et al.

[11] Patent Number: 5,209,775
[45] Date of Patent: May 11, 1993

[54] WATER REPELLENTS CONTAINING ORGANOSILICON COMPOUNDS

[75] Inventors: Howard M. Bank, Freeland; Dipak Narula; Lori A. Stark, both of Midland, all of Mich.

[73] Assignee: Dow Corning Corporation, Midland, Mich.

[21] Appl. No.: 824,271

[22] Filed: Jan. 23, 1992

[51] Int. Cl.⁵ .................................................. C07G 1/06
[52] U.S. Cl. ..................................... 106/2; 106/287.11; 106/287.13; 106/287.16; 524/828; 524/869; 528/12; 528/18; 528/20; 528/22; 528/29; 528/39; 528/38; 427/387; 428/446; 428/447; 428/688; 428/702; 428/703
[58] Field of Search .................. 106/2, 287.11, 287.13, 106/287.16; 524/858, 869; 528/12, 18, 20, 22, 29, 39, 38; 556/413, 410, 446, 465; 427/387; 428/447, 446, 688, 202, 203

[56] References Cited

U.S. PATENT DOCUMENTS

| | | | |
|---|---|---|---|
| 3,649,320 | 3/1972 | Yates | 106/287.11 |
| 4,791,214 | 12/1988 | Mori et al. | 106/287.11 |
| 5,051,129 | 9/1991 | Cuthbert | 106/2 |
| 5,073,195 | 12/1991 | Cuthbert et al. | 106/2 |

*Primary Examiner*—Mark L. Bell
*Assistant Examiner*—C. M. Bonner
*Attorney, Agent, or Firm*—Jim L. DeCesare

[57] ABSTRACT

A composition which is an aqueous solution including (i) an alkyltrialkoxysilane with $C_1$ to $C_6$ alkyl groups on silicon; (ii) a silane coupling agent, (iii) an amino resin, and (iv) a quaternary ammonium silane. The composition is used to render surfaces water repellent.

30 Claims, No Drawings

WATER REPELLENTS CONTAINING ORGANOSILICON COMPOUNDS

BACKGROUND OF THE INVENTION

This invention relates to compositions for rendering surfaces water repellent, and more particularly is directed to aqueous compositions containing certain organosilicon compounds.

The treatment of surfaces such as masonry with compositions containing organosilicon compounds is old in the art. U.S. Pat. No. 5,051,129 issued Sep. 24, 1991 for example teaches that a wide variety of masonry products can be protected from the damaging effects of water penetration by the application of an aqueous solution containing the product obtained by combining water with an alkyltrialkoxysilane such as methyltrimethoxysilane and a silane coupling agent such as N-(2-aminoethyl)-3-aminopropyltrimethoxysilane.

The present invention is an improvement of the '129 patent and provides a surface treating composition which contains in addition to an alkyltrialkoxysilane and a silane coupling agent, certain quaternary ammonium organosilicon compounds and certain amino resins. The compositions of the present invention possess advantages over the compositions of the '129 patent to the extent that surface treatment can be extended to the protection of surfaces such as grout.

SUMMARY OF THE INVENTION

This invention is directed to a surface treating composition capable of rendering a wide variety of surfaces water repellent which is in the form of an aqueous solution containing the product obtained by combining water with an alkyltrialkoxysilane, a water soluble organosilane coupling agent or hydrolysis product thereof, a quaternary ammonium silane, and an amino resin.

The invention is also directed to a surface treating composition capable of rendering a wide variety of surfaces water repellent which is in the form of an aqueous solution containing the product obtained by combining water with an alkyltrialkoxysilane, a quaternary ammonium silane, and an amino resin.

It is an object of the present invention to provide a water repellent composition in the form of an aqueous solution containing the product obtained by combining water with organosilicon compounds and an amino resin which is particularly suitable for the treatment of grout in addition to other types of surfaces.

It is a further object of the present invention to provide a water repellent composition in the form of an aqueous solution containing the produce obtained by combining water with organosilicon compounds and an amino resin which is capable of providing good water exclusion from surfaces treated with the composition, in order that the treated surfaces will exhibit good water beading.

These and other objects, features and advantages of the herein defined present invention will become more apparent from a consideration of the following detailed description thereof.

DETAILED DESCRIPTION OF THE INVENTION

The surface treating composition according to the present invention is formed by mixing together water and three different types of organosilicon compound. Compositions can be formulated from (i) a quaternary ammonium organosilane, (ii) an alkyltrialkoxysilane, and (iii) a water soluble organosilane coupling agent or hydrolysis product thereof. An additional ingredient of the surface treatment compositions of the present invention is an amino resin.

The organosilicon quaternary ammonium compound in accordance with the present invention is an organosilane having a formula selected from the group consisting of:

 (I)

 (II)

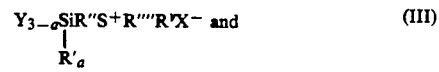 (III)

 (IV)

wherein in each formula (I)–(IV):

Y is RO where R is an alkyl radical of one to four carbon atoms;

a has a value of zero, one or two;

R' is a methyl or ethyl radical;

R" is an alkylene group of one to four carbon atoms;

R''', R'''' and $R^v$ are each independently selected from the group consisting of alkyl radicals of one to eighteen carbon atoms, —$CH_2C_6H_5$, —$CH_2C$-$H_2OH$, —$CH_2OH$, and —$(CH_2)_xNHC(O)R^{vi}$ wherein x has a value of from two to ten and $R^{vi}$ is a perfluoroalkyl radical having from one to twelve carbon atoms;

X is chloride, bromide, fluoride, iodide, acetate or tosylate; and

Z is a positively charged aromatic pyridinium ring of the formula $C_5H_6N^+$—.

These compounds are well known in the art and are shown in numerous domestic and foreign patents assigned to the Dow Corning Corporation, Midland, Mich. USA among which are U.S. Pat. Nos. 4,847,088; 4,865,844; 4,908,355; 4,921,701; 4,985,023; 4,990,338; 5,013,459; 5,019173; and European published Application 355,765. The positively charged aromatic pyridinium ring $C_5H_6N^+$— shown as Z in formula (IV) above is shown structurally in each of those patents.

R in the above formulas are alkyl groups of one to four carbon atoms. Thus, useful as R in this invention are methyl, ethyl, propyl, and butyl radicals. The value of a is zero, one or two, and R' is a methyl or ethyl radical. R" for purposes of the present invention is an alkylene group of one to four carbon atoms. Thus, R" can be alkylene groups such as methylene, ethylene, propylene, and butylene. R''', R'''' and $R^v$ are each independently an alkyl radical of one to eighteen carbon atoms, —$CH_2C_6H_5$, —$CH_2CH_2OH$, —$CH_2OH$, or —$(CH_2)_xNHC(O)R^{vi}$. x has a value of from two to ten and $R^{vi}$ is a perfluoroalkyl radical having from one to twelve carbon atoms. X is chloride, bromide, fluoride, iodide, acetate or tosylate. Z is a positively charged aromatic pyridinium ring of the formula $C_5H_6N^+$—.

Preferred for this invention are the quaternary ammonium organosilanes of the formula

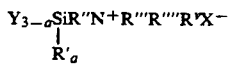

in which R is methyl or ethyl; a has a value of zero; R'' is propylene; R''' is methyl or ethyl; R'''' and R$^v$ are alkyl groups containing one to eighteen carbon atoms wherein at least one such group is larger than eight carbon atoms; and X is either chloride, acetate or tosylate.

Specific quaternary ammonium organosilanes within the scope of the present invention are represented by the formulas:

$(CH_3O)_3Si(CH_2)_3N^+(CH_3)_2C_{18}H_{37}Cl^-$ $(CH_3O)_3Si(CH_2)_3N^+(CH_3)_2C_{18}H_{37}Br^-$ $(CH_3O)_3Si(CH_2)_3N^+(C_{10}H_{21})_2CH_3Cl^-$ $(CH_3O)_3Si(CH_2)_3N^+(C_{10}H_{21})_2CH_3Br^-$ $(CH_3O)_3Si(CH_2)_3N^+(CH_3)_3Cl^-$ $(CH_3O)_3Si(CH_2)_3P^+(C_6H_5)_3Cl^-$ $(CH_3O)_3Si(CH_2)_3P^+(C_6H_5)_3Br^-$ $(CH_3O)_3Si(CH_2)_3P^+(CH_3)_3Cl^-$ $(CH_3O)_3Si(CH_2)_3P^+(C_6H_{13})_3Cl^-$ $(CH_3O)_3Si(CH_2)_3N^+(CH_3)_2C_4H_9Cl^-$ $(CH_3O)_3Si(CH_2)_3N^+(CH_3)_2CH_2C_6H_5Cl^-$ $(CH_3O)_3Si(CH_2)_3N^+(CH_3)_2CH_2CH_2OHCl^-$ $(CH_3O)_3Si(CH_2)_3N^+(C_2H_5)_3Cl^-$ $(CH_3O)_3Si(CH_2)_3C_5H_6N^+Cl^-$ $(C_2H_5O)_3Si(CH_2)_3N^+(CH_3)_2C_{18}H_{37}Cl^-$ $(CH_3O)_3Si(CH_2)_3N^+(CH_3)_2(CH_2)_3NH-C(O)(CF_2)_6CF_3Cl^-$

One of the most preferred species of quaternary ammonium compounds corresponding to formula (I) is 3-(trimethoxysilyl)propyldimethyloctadecyl ammonium chloride of the formula:

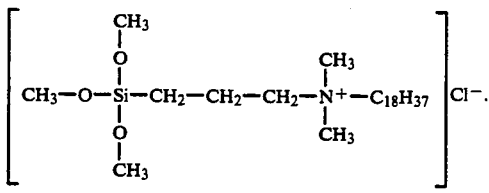

This compound will be referred to hereinafter as "TMS" for the sake of simplicity.

Alkyltrialkoxysilanes suitable for use in the compositions in accordance with the present invention are (i) an alkyltrialkoxysilane having $C_1$ to $C_6$ alkyl groups on silicon or (ii) a blend of alkyltrialkoxysilanes each having $C_1$ to $C_6$ alkyl groups on silicon. Such silanes are well known in the art and are commercially available materials. Representative examples of such silanes are methyltrimethoxysilane, ethyltrimethoxysilane, propyltrimethoxysilane, isopropyltrimethoxysilane, butyltrimethoxysilane, isobutyltrimethoxysilane, pentyltrimethoxysilane and hexyltrimethoxysilane. The corresponding alkyltriethoxysilanes may also be employed. Methyltrimethoxysilane and isobutyltrimethoxysilane are the most preferred alyltrialkoxysilanes for use in the present invention.

Organosilane coupling agents are known in the art as evidenced by U.S. Pat. No. 4,689,085 issued Aug. 25, 1987. Silane coupling agents have the structure $X_3Si(CH_2)_nY$ in which n has a value of from zero to three; X is a hydrolyzable group on silicon; and Y is a reactive organofunctional group. Examples of some known commercial silane coupling agents suitable for use as an ingredient of the surface treating compositions in accordance with the present invention are N-(2-aminoethyl)-3-aminopropyltrimethoxy silane; N-(aminoethylaminomethyl)phenyltrimethoxy silane; N-(2-aminoethyl)-3-aminopropyltris(2-ethylhexoxy) silane; 3-aminopropyltrimethoxysilane; trimethoxysilylpropyldiethylenetriamine; phosphonate silanes and their salts such as propylmethylphosphinatetrimethoxysilane and its salt sodium (trihydroxysilyl) propylmethylphosphonate; and bis(2-hydroxyethyl)-3-aminopropyltrimethoxysilane. The silane coupling agent most preferred for use in the present invention is N-(2-aminoethyl)-3-aminopropyltrimethoxy silane.

Amino resins are thermosetting polymers manufactured by combining an aldehyde with a compound containing an amino group (—NH$_2$). Most amino resins are based on the reaction of formaldehyde with urea or melamine. The two primary commercially important amino resins are urea-formaldehyde resins and melamine-formaldehyde resins. Many such amino resins are manufactured by American Cyanamid Company, Wayne, N.J. under the trademark BEETLE ®. Formaldehyde is difunctional and capable of linking two molecules together. Urea and melamine are difunctional in that each has two replaceable hydrogen atoms that can react with formaldehyde. Since urea and melamine contain two and three amino groups, they react polyfunctionally with formaldehyde to form three dimensional crosslinked polymers. The amino resin most preferred in accordance with the present invention is a high solids (eighty-eight percent) water soluble urea-formaldehyde resin sold by the American Cyanamid Company under the trademark BEETLE ® 60.

The compositions in accordance with the present invention can be employed in the treatment of various surfaces encompassing concrete and masonry products, textiles, paper, paperboard, leather products, and cellulosic materials. Examples of leather products are garments, shoes and boots. Textiles include awnings, tents, tarpaulins, rainwear, covers, slickers, canvas, asbestos, fiberglass, natural fibers, peat moss, natural and synthetic yarns, woven and nonwoven materials, carpets and carpet fibers. Cellulosic materials contemplated herein for treatment include wood, wood products, fiberboard, cedar, redwood, firs, plywood, and structural timbers. Concrete and masonry surfaces which may be treated include products and surfaces of heavy and light weight concrete, gypsum, concrete blocks, cinder blocks, soft mud bricks, sand lime bricks, drain tiles, ceramic tiles, sandstone, plaster, clay bricks, natural stones and rocks, roofing tiles, calcium silicate bricks, asbestos cement, slag stones and bricks, stucco, limestone, macadam, marble, grout, mortar, terrazzo, clinker, pumice, terra cotta, porcelain, adobe, coral, dolomite and asphalt. Noncementitious surfaces may be treated with the compositions of the present invention including perlite, cellular glass, vermiculite, mica and diatomaceous earth. Representative of such materials in the examples set forth below are (i) a neutral cementitious sandstone; (ii) a basic cementitious material which was grout; and (iii) a cellulosic material which was wood in the form of pine, redwood and cedar.

The compositions in accordance with the present invention are formulated as aqueous solutions containing the product obtained by combining water with the various organosilicon compounds and the amino resin. These aqueous solutions comply with various of the local, state and federal regulations regarding volatile organic content (VOC). Such regulations typically prohibit a volatile organic content for an architectural coating for example in excess of about four hundred grams per liter. In contrast, many coatings of the prior art containing solvent based alkoxysilanes liberate an alcohol which is a volatile organic compound. The volatile organic content (VOC) of such prior art solvent based coatings can be of the order of magnitude of 650–700 grams per liter.

Volatile Organic Content (VOC) has been defined as the amount of volatile organic compounds liberated from a coating as determined by ASTM D3690 and EPA Reference Method 24 which are standard industrial tests. Under the definition, a volatile organic compound is any compound which enters the atmosphere and photochemically reacts in the atmosphere with nitrogen oxides to reduce ozone. Reduction of VOC has been mandated in several states and regulations in California for example require less than four hundred grams of volatiles per liter of product to enter the atmosphere. This can be determined by baking 0.5–10.0 grams of a product in an oven at one hundred-ten degrees Centigrade for one hour. The amount of solids which remain is subtracted from the total of the ten grams which was tested. Calculations are based on the weight of the volatiles that have evaporated which is reported as grams per liter.

Examples illustrating the concept of the present invention are set forth below. The water repellency of the surfaces treated with the compositions of the present invention is shown in the tables as "water exclusion". The procedures employed for the purpose of determining water exclusion are set forth immediately below.

TEST PROCEDURES

Standard 2×4 pine, redwood, and cedar were obtained from a local lumber supply, cut to six inches length, and allowed to equilibrate at room temperature in a 50% relative humidity atmosphere. The boards were treated by brushing on until saturated or soaking for three minutes in the water repellent solution. A control board was left untreated and kept in the 50% humidity room during the entire cure process. The treated boards were left to cure for one day in a laboratory atmosphere and placed in the 50% humidity room for six days to finish the cure and equilibrated to 50% humidity. After cure, all boards including the control were weighed and placed in room temperature water for 15 minutes, turned over and left another 15 minutes. After 30 minutes in water, all boards were weighed and the water uptake calculated. The water exclusion was (water uptake of control—water uptake of treated board)×100/(water uptake of control).

The Federal test method SS-W-110C was used to obtain percent water adsorption of each piece of grout and sandstone. The grout cubes used in the testing were 2"×2"×2" cubes made from mortar and sand. The standstone pieces were 1"×1"×4" made of Briar Hill Sandstone. An untreated control was included for comparison and to calculate water exclusion. Grout and standstone pieces were wire brushed and blown clean with high pressure air. The pieces were weighed and dried in an oven at 80° C. until a constant weight was reached. The pieces were weighed, placed in ¼" of water for 24 hours, weighed again, and dried in an 80° C. oven until a constant weight was reached. The pieces were treated with the water repellent by soaking for 10 seconds. The pieces were weighed before and after treatment. The pieces were allowed to cure 48 hours before being returned to ¼" of water to soak for 72 hours. After soaking, the pieces were weighed again. Water uptake, percent water adsorption (water uptake×100/weight of piece dry), and % water exclusion were calculated. However, in Examples IV–VIII the grout and sandstone were not preconditioned in the oven and ¼" of water before treatment.

A series of experiments were performed to determine water repellent properties. Three types of substrates were treated: a neutral cementitious sandstone; a basic cementitious grout; and cellulosic material wood.

EXAMPLE I

There was prepared a dimer of two methoxy silanes which were methyltrimethoxysilane (I) and N-(2-aminoethyl)-3-aminopropyltrimethoxysilane (II). The dimer was produced by combining 2.7 moles of (I) and 1.4 moles of (II) and adding 1.8 moles of water slowly to the silane combination. This partial hydrolysis product was stripped of methanol under vacuum along with a small amount of I. The Dimer which resulted contained about 60–65% by weight of active material and was stable upon dilution in water to between 0.5% to 20% by weight active. The concentrations tested were 2.5%, 5%, 10%, and 15%. The results in Table I were obtained on sandstone and wood. The water exclusion was calculated as (water pickup of untreated substrate—water pickup of treated substrate)×100/(water pickup of untreated substrate).

TABLE I

| Substrate | % Active | % Water Exclusion |
|---|---|---|
| Sandstone | 2.5 | 89 |
|  | 5.0 | 90 |
|  | 10.0 | 88 |
| 6" Pine 2 × 4 | 2.5 | 19 |
|  | 5.0 | 26 |
|  | 10.0 | 38 |
|  | 15.0 | 54 |

EXAMPLE II

The ratios in Example I of the silanes methyltrimethoxsilane (I) and N-(2-aminoethyl)aminopropyltrimethoxysilane (II) were changed to one mole of each silane with 1.29 moles of water to reduce the amount of silane (I) stripped off with methanol. This material will be referred to hereinafter as the "Dimer". The water exclusion improved on pine and was similar as Example I on sandstone as shown in Table II.

TABLE II

| Substrate | % Active | % Water Exclusion |
|---|---|---|
| Sandstone | 2.5 | 90 |
|  | 5.0 | 87 |
|  | 10.0 | 88 |
| 6" Pine 2 × 4 | 2.5 | 65 |
|  | 5.0 | 70 |
|  | 10.0 | 70 |

Neither coating provided good water exclusion on grout cubes.

EXAMPLE III

The quaternary ammonium silane compound TMS was added to the "Dimer" in a ratio of 75/25 to provide a material containing about 70% by weight actives. The material was diluted with water.

EXAMPLE IV

A high solids (88%) urea-formaldehyde water soluble resin (Beetle ® 60) was added in varying amounts to the material described in Example III. The material was diluted with water to 5% by weight active. The water exclusions achieved are shown in Table III.

TABLE III

| Substrate | % Resin | % Active | % Water Exclusion |
|---|---|---|---|
| Pine | 5 | 5.0 | 63.3 |
|  | 10 | 5.0 | 63.9 |
|  | 20 | 5.0 | 60.5 |
| Grout | 5 | 5.0 | 49.5 |
|  | 10 | 5.0 | 5.3 |
|  | 20 | 5.0 | 0 |
| Sandstone | 5 | 5.0 | 25.7 |
|  | 10 | 5.0 | −25 |
|  | 20 | 5.0 | −4 |

EXAMPLE V

The water exclusion in Example IV was improved by preparing the following repellent combination: 2.235% "Dimer", 2.235% TMS; 2.235% high solids urea-formaldehyde resin (Beetle ® 60), and 93.29% by weight water. This material was diluted in water and results are shown in Table IV.

TABLE IV

| Substrate | % Active | % Water Exclusion |
|---|---|---|
| Pine | 5.0 | 73 |
| Grout | 5.0 | 55 |
| Sandstone | 5.0 | 15 |

EXAMPLE VI

The following formulation produced a water repellent for wood and concrete substrates: 1.195% N-(2-aminoethyl)-3-aminopropyltrimethoxysilane, 1.195% methyltrimethoxysilane, 2.39% TMS, 2.39% high solids urea-formaldehyde resin (Beetle ® 60), and 92.8% by weight water. The water exclusion on a 6" pine 2×4 was 73.7%, and 55.3% on a grout cube.

EXAMPLE VII

The following cold blend mixture produced a water repellent coating: 2.56% methyltrimethoxysilane, 2.56% TMS, 2.56% high solids urea-formaldehyde resin (Beetle ® 60), and 92.33% by weight water. The water exclusion was 87.32% on pine, 51.8% on grout, and 34.6% on sandstone.

EXAMPLE VIII

Isobutyltrimethoxysilane was mixed with a urea-formaldehyde resin and the compound TMS in the following percentages: 2.34% isobutyltrimethoxysilane, 2.34% TMS, 2.34% high solids urea-formaldehyde resin (Beetle ® 60), and 92.98% by weight water. The water exclusion results were obtained on wood, grout, and sandstone, and are shown in Table V.

TABLE V

| Substrate | % Water Exclusion |
|---|---|
| Sandstone | 35.5 |
| Grout | 55.2 |
| Pine | 78.9 |

EXAMPLE IX

A trimethoxy phosphonate silane was used to achieve a water reducible isobutyltrimethoxysilane material with the following composition: 3.56% isobutyltrimethoxysilane; 0.3% propylmethylmethylphospinatetrimethoxysilane; 3.55% TMS; and 92.59% water. The material was applied to pine, grout, and sandstone and tested for water exclusion as shown in Table VI.

TABLE VI

| Substrate | % Water Exclusion |
|---|---|
| Sandstone | 56.8 |
| Grout | 54.4 |
| Pine | 80.5 |

EXAMPLE X

The phosphonate salt of the silane phosphonate of Example IX was added to the "Dimer" to provide a water soluble material. The following composition was cold blended: 5% "Dimer"; 91% water; and 4% sodium (trihydroxysilyl) propylmethylphosphate 50% in water. The material was applied to pine, sandstone and grout and tested for water exclusion as shown in Table VII.

TABLE VII

| Substrate | % Water Exclusion |
|---|---|
| Sandstone | 80.2 |
| Grout | 0 |
| Pine | 73.0 |

The compositions of this invention may be formulated as water solutions by combining together from (i) zero to fifty percent by weight of an alkyltrialkoxysilane and a water soluble silane coupling agent or hydrolysis product thereof which are combined in a ratio of from 0.5:1.0 to 3.0:1.0; (ii) zero to fifty percent by weight of a quaternary ammonium silane; (iii) zero to twenty percent by weight of an amino resin; and (iv) the balance water.

It will be apparent from the foregoing that many other variations and modifications may be made in the compounds, compositions and methods described herein without departing substantially from the essential features and concepts of the present invention. Accordingly, it should be clearly understood that the forms of the invention described herein are exemplary only and are not intended as limitations on the scope of the present invention as defined in the appended claims.

That which is claimed is:

1. A composition comprising the product obtained by combining water, (i) an alkyltrialkoxysilane selected from the group consisting of alkyltrialkoxysilanes with $C_1$ to $C_6$ alkyl groups on silicon and blends of alkyltrialkoxysilanes with $C_1$ to $C_6$ alkyl groups on silicon, (ii) a water soluble silane coupling agent or hydrolysis product thereof, (iii) an amino resin, and (iv) a quaternary ammonium silane having a formula selected from the group consisting of:

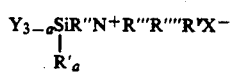 (I)

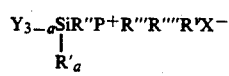 (II)

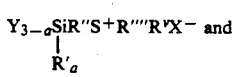 and (III)

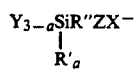 (IV)

wherein in each formula (I)-(IV):

Y is RO where R is alkyl radical of one to four carbon atoms;

a has a value of zero, one or two;

R' is a methyl or ethyl radical;

R'' is an alkylene group of one to four carbon atoms;

R''', R'''' and $R^V$ are each independently selected from the group consisting of alkyl radicals of one to eighteen carbon atoms, $-CH_2C_6H_5$, $-CH_2CH_2OH$, $-CH_2OH$, and $-(CH_2)_xNHC(O)R^{vi}$ wherein x has a value of from two to ten and $R^{vi}$ is a perfluoroalkyl radical having from one to twelve carbon atoms;

X is chloride, bromide, fluoride, iodide, acetate or tosylate; and

Z is a positively charged aromatic pyridinium ring of the formula $C_5H_6N^+-$.

2. A composition according to claim 1 in which the quaternary ammonium silane has the formula

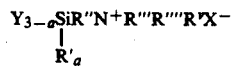

in which R is methyl or ethyl; a has a value of zero; R'' is propylene; R''' is methyl or ethyl; R'''' and $R^v$ are alkyl groups containing one to eighteen carbon atoms wherein at least one such group is larger than eight carbon atoms; and X is chloride, acetate or tosylate.

3. A composition according to claim 2 in which the quaternary ammonium silane is the compound 3-(trimethoxysilyl)propyldimethyloctadecyl ammonium chloride of the formula

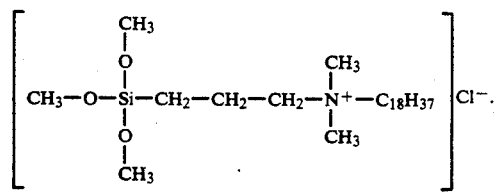

4. A composition according to claim 1 in which the alkyltrialkoxysilane is selected from the group consisting of methyltrimethoxysilane, ethyltrimethoxysilane, propyltrimethoxysilane, isopropyltrimethoxysilane, butyltrimethoxysilane, isobutyltrimethoxysilane, pentyltrimethoxysilane and hexyltrimethoxysilane.

5. A composition according to claim 4 in which the alkyltrialkoxysilane is methyltrimethoxysilane.

6. A composition according to claim 4 in which the alkyltrialkoxysilane is isobutyltrimethoxysilane.

7. A composition according to claim 1 in which the silane coupling agent has the formula $X_3Si(CH_2)_nY$ in which n has a value of from zero to three; X is a hydrolyzable group on silicon; and Y is a reactive organofunctional group.

8. A composition according to claim 7 in which the silane coupling agent is selected from the group consisting of N-(2-aminoethyl)-3-aminopropyltrimethoxy silane;
N-(aminoethylaminomethyl)phenyltrimethoxy silane;
N-(2-aminoethyl)-3-aminopropyltris(2-ethylhexoxy) silane;
3-aminopropyltrimethoxysilane;
trimethoxysilylpropyldiethylenetriamine;
propylmethylphosphinatetrimethoxysilane;
sodium (trihydroxysilyl) propylmethylphosphonate; and
bis(2-hydroxyethyl)-3-aminopropyltrimethoxysilane.

9. A composition according to claim 8 in which the silane coupling agent is
N-(2-aminoethyl)-3-aminopropyltrimethoxy silane.

10. A composition according to claim 1 in which the amino resin is selected from the group consisting of urea-formaldehyde resins and melamine-formaldehyde resins.

11. A composition according to claim 10 in which the amino resin is a water soluble urea-formaldehyde resin.

12. A composition comprising the product obtained by combining water, (i) an alkyltrialkoxysilane selected from the group consisting of alkyltrialkoxysilanes with $C_1$ to $C_6$ alkyl groups on silicon and blends of alkyltrialkoxysilanes with $C_1$ to $C_6$ alkyl groups on silicon, (ii) an amino resin, and (iii) a quaternary ammonium silane having a formula selected from the group consisting of:

 (I)

 (II)

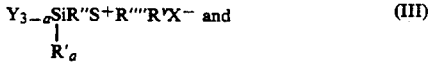 and (III)

-continued

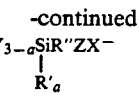

wherein in each formula (I)–(IV):
Y is RO where R is an alkyl radical of one to four carbon atoms;
a has a value of zero, one or two;
R' is a methyl or ethyl radical;
R" is an alkylene group of one to four carbon atoms;
R''', R'''' and R$^v$ are each independently selected from the group consisting of alkyl radicals of one to eighteen carbon atoms, —CH$_2$C$_6$H$_5$, —CH$_2$CH$_2$OH, —CH$_2$OH, and —(CH$_2$)$_x$NHC(O)R$^{vi}$ wherein x has a value of from two to ten and R$^{vi}$ is a perfluoroalkyl radical having from one to twelve carbon atoms;
X is chloride, bromide, fluoride, iodide, acetate or tosylate; and
Z is a positively charged aromatic pyridinium ring of the formula C$_5$H$_6$N$^+$—.

13. A composition according to claim 12 in which the quaternary ammonium silane has the formula

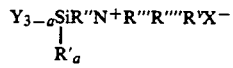

in which R is methyl or ethyl; a has a value of zero; R" is propylene; R''' is methyl or ethyl; R'''' and R$^v$ are alkyl groups containing one to eighteen carbon atoms wherein at least one such group is larger than eight carbon atoms; and X is chloride, acetate or tosylate.

14. A composition according to claim 13 in which the quaternary ammonium silane is the compound 3-(trimethoxysilyl)propyldimethyloctadecyl ammonium chloride of the formula

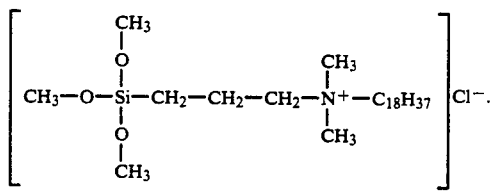

15. A composition according to claim 12 in which the alkyltrialkoxysilane is selected from the group consisting of methyltrimethoxysilane, ethyltrimethoxysilane, propyltrimethoxysilane, isopropyltrimethoxysilane, butyltrimethoxysilane, isobutyltrimethoxysilane, pentyltrimethoxysilane and hexyltrimethoxysilane.

16. A composition according to claim 15 in which the alkyltrialkoxysilane is methyltrimethoxysilane.

17. A composition according to claim 15 in which the alkyltrialkoxysilane is isobutyltrimethoxysilane.

18. A composition according to claim 12 in which the amino resin is selected from the group consisting of urea-formaldehyde resins and melamine-formaldehyde resins.

19. A composition according to claim 18 in which the amino resin is a water soluble urea-formaldehyde resin.

20. A method of treating a surface in order to render the surface water repellent comprising applying to the surface to be treated in aqueous solution formed by combining water, (i) an alkyltrialkoxysilane selected from the group consisting of alkyltrialkoxysilanes with C$_1$ to C$_6$ alkyl groups on silicon and blends of alkyltrialkoxysilanes with C$_1$ to C$_6$ alkyl groups on silicon, (ii) an amino resin, and (iii) a quaternary ammonium silane having a formula selected from the group consisting of:

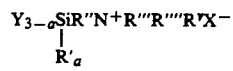

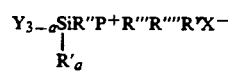

 and

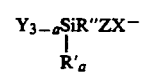

wherein in each formula (I)–(IV):
Y is RO where R is an alkyl radical of one to four carbon atoms;
a has a value of zero, one or two;
R' is a methyl or ethyl radical;
R" is an alkylene group of one to four carbon atoms;
R''', R'''' and R$^v$ are each independently selected from the group consisting of alkyl radicals of one to eighteen carbon atoms, —CH$_2$C$_6$H$_5$, —CH$_2$CH$_2$OH, —CH$_2$OH, and —(CH$_2$)$_x$NHC(O)R$^{vi}$ wherein x has a value of from two to ten and R$^{vi}$ is a perfluoroalkyl radical having from one to twelve carbon atoms;
X is chloride, bromide, fluoride, iodide, acetate or tosylate; and
Z is a positively charged aromatic pyridinium ring of the formula C$_5$H$_6$N$^+$—.

21. A method according to claim 20 in which the quaternary ammonium silane has the formula

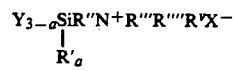

in which R is methyl or ethyl; a has a value of zero; R" is propylene; R''' is methyl or ethyl; R'''' and R$^v$ are alkyl groups containing one to eighteen carbon atoms wherein at least one such group is larger than eight carbon atoms; and X is chloride, acetate or tosylate.

22. A method according to claim 21 in which the quaternary ammonium silane is the compound 3-(trimethoxysilyl)propyldimethyloctadecyl ammonium chloride of the formula

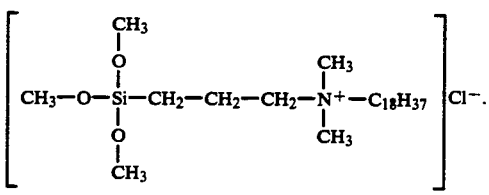

23. A method according to claim 20 in which the alkyltrialkoxysilane is selected from the group consisting of methyltrimethoxysilane, ethyltrimethoxysilane, propyltrimethoxysilane, isopropyltrimethoxysilane, butyltrimethoxysilane, isobutyltrimethoxysilane, pentyltrimethoxysilane and hexyltrimethoxysilane.

24. A method according to claim 23 in which the alkyltrialkoxysilane is methyltrimethoxysilane.

25. A method according to claim 23 in which the alkyltrialkoxysilane is isobutyltrimethoxysilane.

26. A method according to claim 20 in which the amino resin is selected from the group consisting of urea-formaldehyde resins and melamine-formaldehyde resins.

27. A method according to claim 26 in which the amino resin is a water soluble urea-formaldehyde resin.

28. A method according to claim 20 in which the surface to be treated is grout.

29. A method according to claim 20 in which the aqueous solution includes a silane coupling agent selected from the group consisting of
N-(2-aminoethyl)-3-aminopropyltrimethoxy silane;
N-(aminoethylaminomethyl)phenyltrimethoxy silane;
N-(2-aminoethyl)-3-aminopropyltris(2-ethylhexoxy) silane;
3-aminopropyltrimethoxysilane;
trimethoxysilylpropyldiethylenetriamine;
propylmethylphosphinatetrimethoxysilane;
sodium (trihydroxysilyl) propylmethylphosphonate; and
bis(2-hydroxyethyl)-3-aminopropyltrimethoxysilane.

30. A method according to claim 29 in which the silane coupling agent is
N-(2-aminoethyl)-3-aminopropyltrimethoxy silane.

* * * * *